United States Patent [19]

Rembaum et al.

[11] 4,224,198
[45] Sep. 23, 1980

[54] PROTEIN SPECIFIC POLYMERIC IMMUNOMICROSPHERES

[75] Inventors: Alan Rembaum; Shiao-Ping S. Yen; William J. Dreyer, all of Altadena, Calif.

[73] Assignee: California Institute of Technology, Pasadena, Calif.

[21] Appl. No.: 909,804

[22] Filed: May 26, 1978

Related U.S. Application Data

[62] Division of Ser. No. 634,935, Nov. 24, 1975, Pat. No. 4,138,383.

[51] Int. Cl.² ............................................. C08L 89/00
[52] U.S. Cl. ........................................ 260/8; 424/55; 424/12
[58] Field of Search ............................... 260/8; 424/12

[56] References Cited

U.S. PATENT DOCUMENTS 4,138,383  2/1979  Rembaum et al. .................. 526/227

Primary Examiner—Edward M. Woodberry
Attorney, Agent, or Firm—Doms, Smith, Lande & Rose

[57] ABSTRACT

Small, round, bio-compatible microspheres capable of covalently bonding proteins and having a uniform diameter below about 3500 Å are prepared by substantially instantaneously initiating polymerization of an aqueous emulsion containing no more than 35% total monomer including an acrylic monomer substituted with a covalently bondable group such as hydroxyl, amino or carboxyl and a minor amount of a cross-linking agent.

18 Claims, 3 Drawing Figures

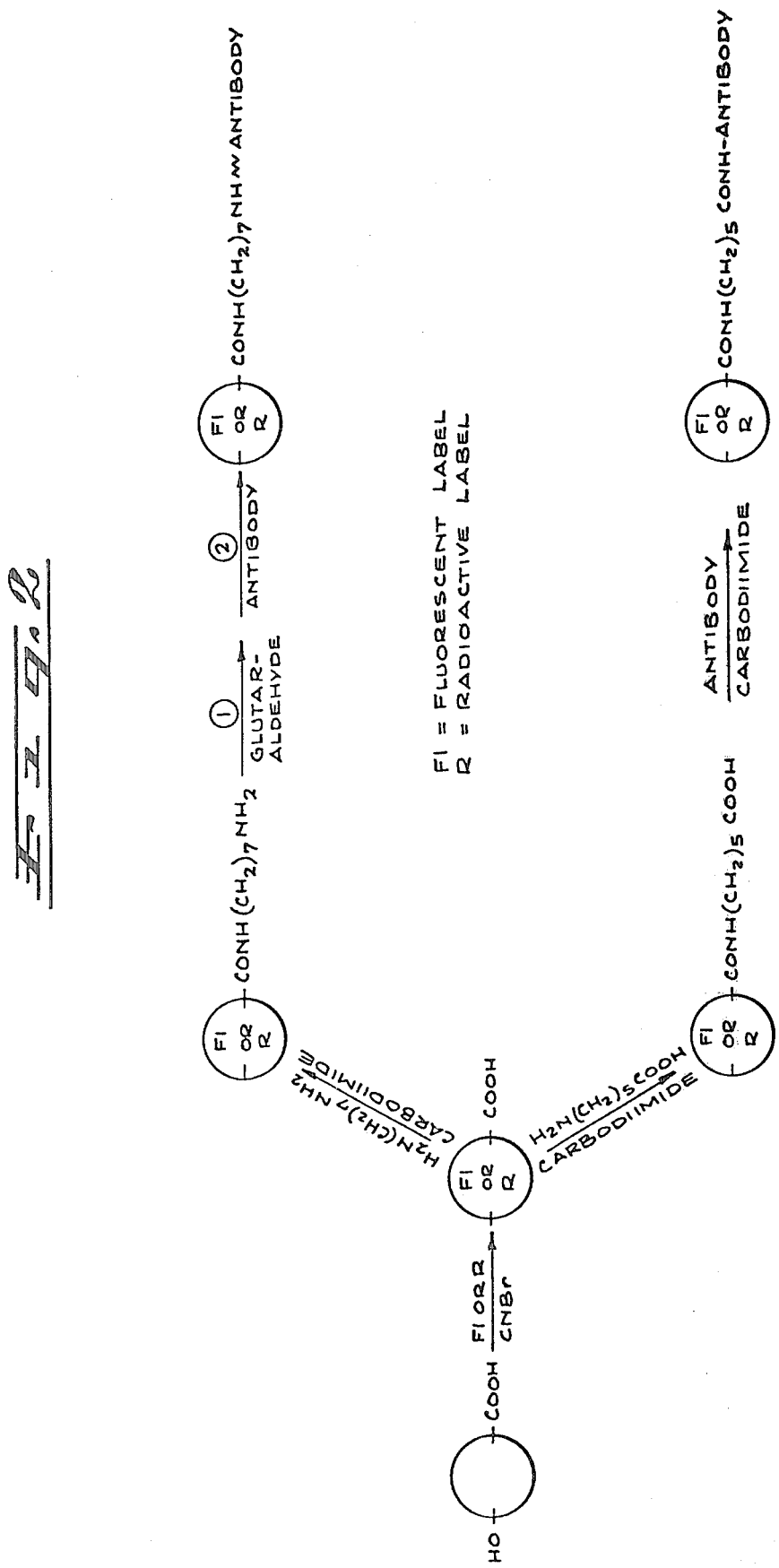

PROTEIN SPECIFIC POLYMERIC IMMUNOMICROSPHERES

ORIGIN OF THE INVENTION

The invention described herein was made in the performance of work under a NASA contract and is subject to the provisions of Section 305 of the National Aeronautics and Space Act of 1958, Public Law 83-568 (72 Stat. 435; 42 USC 2457).

This is a division, of application Ser. No. 634,935, filed Nov. 24, 1975 now issued on Feb. 6, 1973, as U.S. Pat. No. 4,138,383.

BACKGROUND OF THE INVENTION

1. Field of the Invention

The present invention relates to uniformly, sized, polymeric microspheres, to methods of making the microspheres and to their use in labelling cell surfaces.

2. Description of the Prior Art

The isolation and characterization of cell membranes and their components is essential for an understanding of the role in which surface membranes play in regulating a wide variety of biological and immunological activities. The present techniques used for this purpose are not quite satisfactory.

Knowledge of the nature, number and distribution of specific receptors on cell surfaces is of central importance for an understanding of the molecular basis underlying such biological phenomena as cell-cell recognition in development, cell communication and regulation by hormones and chemical transmitters, and differences in normal and tumor cell surfaces. In previous studies, the localization of antigens and carbohydrate residues on the surface of cells, notably red blood cells and lymphocytes, has been determined by bonding antibodies or lectins to such macromolecules as ferritin, hemocyanin or peroxidase which have served as markers for transmission electron microscopy. With advances in high resolution scanning electron microscopy (SEM), however, the topographical distribution of molecular receptors on the surfaces of cell and tissue specimens can be readily determined by similar histochemical techniques using newly developed markers resolvable by SEM.

Recently commercially available polystyrene latex particles have been utilized as immunologic markers for use in the SEM technique. The surface of such polystyrene particles is hydrophobic and hence certain types of macromolecules such as antibodies are absorbed on the surface under carefully controlled conditions. However, such particles stick non-specifically to many surfaces and molecules and this seriously limits their broad application.

The preparation of small, stable spherical particles which are bio-compatible, i.e., do not interact non-specifically with cells or other biological components and which contain functional groups to which specific proteins and other bio-chemical molecules can be covalently bonded is disclosed in copending application Ser. No. 434,124, filed Jan. 17, 1974 now issued on May 18, 1976, as U.S. Pat. No. 3,957,741.

The hydroxyl or amino groups can be activated by cyanogen bromide for covalent bonding of proteins and other chemicals containing amino groups to the polymeric latex. Methacrylic acid residues which impart a negative charge onto the particles are likely to prevent non-specific binding to cell surfaces and to provide carboxyl groups to which a variety of bio-chemical molecules can be covalently bonded using the carbodiimide method. Cross-linking of the polymeric matrix is essential to maintain the stability and size of the particles in both aqueous solution and in organic solvents commonly used in the fixation and dehydration of biological specimens for electron or light microscopy.

However, the suspension polymerization technique disclosed in U.S. Pat. No. 3,957,741 resulted in microspheres having a diameter from 0.1 to 2 microns. Cells, such as red blood cells, have a diameter of about 6 to 10 microns. These microspheres are too large for detection of all or most receptor sites.

SUMMARY OF THE INVENTION

Uniformly sized suspensions of round microspheres having covalent bondable sites and having a selected uniform diameter below 3500 Å and, preferably from 100 Å to 2000 Å are provided in accordance with the invention. The cross-linked beads, being considerably smaller than the biological cells can be custom synthesized to closely match the size of the receptor site. The beads when covalently bound to a protein conjugate can be utilized to label a specific receptor site on the cell membrane.

The microspheres will find use in lectin, antibody or sugar derivatized forms. They can be used to isolate membrane fragments enriched for the appropriate cellular ligand(s) which bind to the substance covalently attached to the bead.

The microspheres can be utilized to yield a biochemical mapping of the membrane with respect to assessment of surface receptors which can redistribute in the plane of the membrane in response to a matrix containing rigidly displayed ligands. This will be useful in determining the contributing roles of the restriction of movement of certain surface receptors to oncogenic transformation of cells. Other applications include the isolation of differentiated regions of cell surface membranes, and studies of this nature would be of great utility in areas such as development biology.

The uniformly small sized microspheres are synthesized by the substantially instantaneous free radical initiated aqueous emulsion polymerization containing a very dilute total monomer content, suitably from 0.5 to 35% and preferably from 3% to about 20% by weight. The microspheres are hydrophilic, hydrolytically stable, are biocompatible and of sufficient mechanical strength for biological applications. The microspheres are of well characterized structure, of outstanding purity and the hydrophilic properties, size and mechanical properties can be systematically varied by selection of monomer and polymerization conditions.

The microspherical beads containing hydroxyl or amine groups covalently bond to antibodies and other biological materials and are useful as specific cell surface markers for scanning electron microscopy. The particles are found to bind to hormones, toxins, lectins, and other molecules and have application in the detection and localization of a variety of cell surface receptors. Particles tagged with fluorescent dye or radioactive molecules serve as sensitive markers for fluorescent microscopy and as reagents for quantitative study of cell surface components. By covalently bonding lectins, antigens, hormones and other molecules to these spheres, detection and localization of specific carbohydrate residues, antibodies, hormone receptors and other specific cell surface components can also be determined. These reagents also have application in highly sensitive radioimmune assays, as visual markers for fluorescent and transmission electron microscopy, for radioactive quantitation of specific cell surface receptors and as potential therapeutic reagents.

These and other attendant advantages of the invention will become apparent as the invention becomes better understood by reference to the following detailed description when considered in conjunction with the accompanying drawings.

BRIEF DESCRIPTION OF THE DRAWINGS

FIG. 2 is a series of curves illustrating the effect of rabbit IgG concentration on the bonding of [125 I] rabbit IgG to 600 Å diameter latex spheres.

DESCRIPTION OF THE PREFERRED EMBODIMENTS

Figure 1:
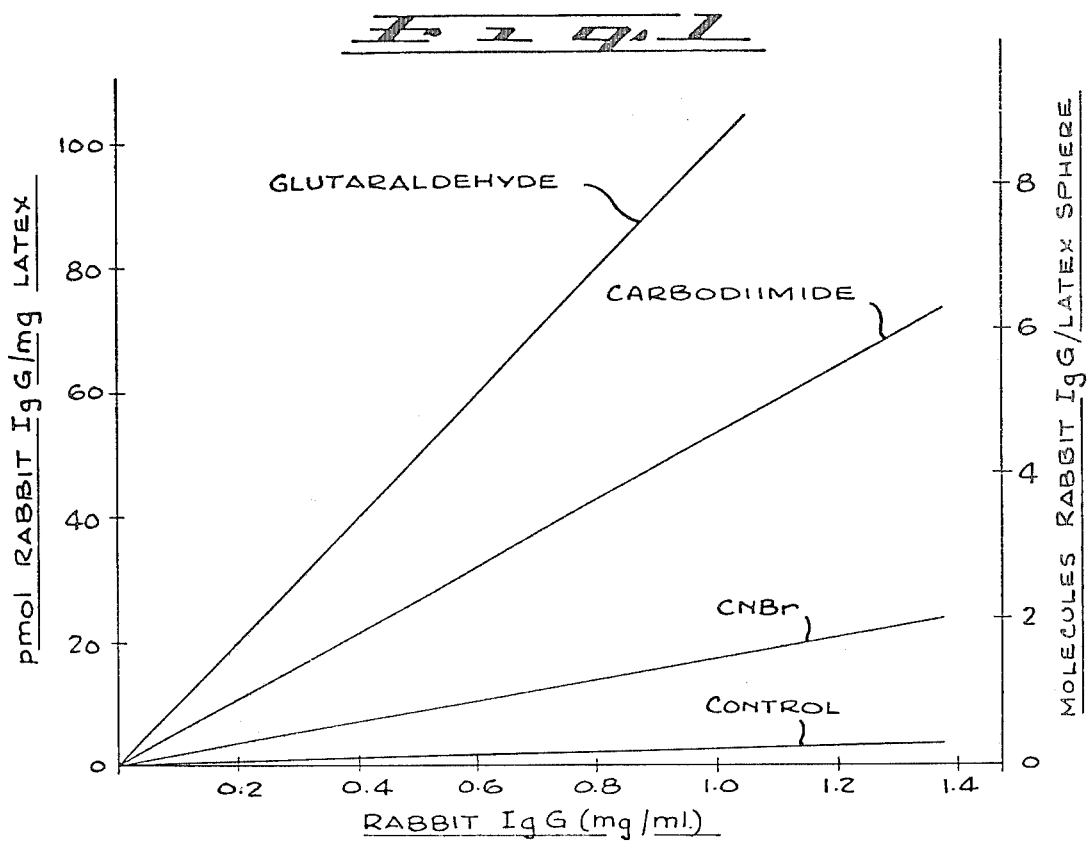
FIG. 1 is a reaction scheme depicting the sequence of reactions used to prepare radioactive (R) and fluorescent (F1) labeled latex-antibody conjugates for all surface labeling studies.

The composition of the monomer mixture is essential to obtain beads of the desired characteristics. The monomers should be substantially water-soluble under the conditions of polymerization such that oil droplets do not form as in conventional emulsion polymerization in order to form the extremely fine, (less than 300 Å) uniformly-shaped beads.

The covalently bondable monomers utilized are freely water soluble and should comprise from 25–50% by weight of the monomer mixture. These monomers are suitably selected from amino, carboxyl or hydroxyl substituted acrylic monomers. Exemplary monomers are acrylamide, acrylic acid, methacrylic acid, or hydroxyl-lower alkyl- or amino lower alkyl acrylates such as those of the formula:

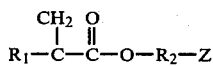

where $R^1$ is hydrogen or lower alkyl of 1–8 carbon atoms, $R^2$ is alkylene of 1–12 carbon atoms, and Z is OH or $R^3$—N—$R^4$ where $R^3$ or $R^4$ are H, lower alkyl or lower alkoxy of 1–8 carbon atoms. 2-hydroxyethyl methacrylate, 3-hydroxypropyl methacrylate, 2-dimethyl-aminoethyl methacrylate and 2-aminoethyl methacrylate are readily available commercially.

The cross-linking agent is present in the monomer mixture in an amount from 5 to 20% by weight, preferably 6–12%, and is a liquid polyunsaturated compound such as a diene or a triene capable of addition polymerization with the unsaturated group of the monomer. Suitable compounds are low molecular weight liquid polyvinyl compounds such as ethylene dimethyacrylate, divinyl benzene, trimethylol propane trimethacrylate, N, N'-methylene-bis-acrylamide, piperazineethylmethacrylate.

A commercial form (95%) of hydroxyethylmethacrylate (HEMA) and hydroxypropyl methacrylate (HPMA) as supplied, contains small amounts of methacrylic acid, hydroxyalkoxyalkylmethacrylate and dimethacrylates-ethylene dimethacrylate in HEMA and propylene dimethacrylate in HPMA. HPMA is generally a mixture in which the principal monomers comprise 68–75% of 2-hydroxypropyl and 25–32% of 1-methyl-2-hydroxyethylmethacrylate. Typical compositions in weight percentage follow:

| Compound | HEMA-94% | HPMA-94% |
| --- | --- | --- |
| Hydroxyalkylmethacrylate | 86 | 87 |
| Higher boiling methacrylate, principally hydroxyalkoxy-alkylmethacrylate | 6 | 5 |
| Methacrylic Acid | 3.5 | 4.5 |
| Dimethacrylate | 1.5 | 0.7 |

The monomer mixture should contain a large percentage, suitably from 40–70% of sparingly water soluble monomers having hydrophobic characteristics since this is found to result in freely suspended individual beads. In absence of such monomers, the polymer is too water soluble and the resultant product is a gel of aggregated soft particles. The cross-linking agent is sparingly soluble. Hydrophobic characteristics can be provided with monomers such as styrene, vinyl toluene or lower alkyl acrylates suitably methyl methacrylate or ethyl methacrylate.

The amount of free radical catalyst also influences the size of the beads for a given monomer concentration. As the amount of catalyst is increased the size of the beads decreases. However, the reaction at increased catalyst level becomes too fast to control causing uneven size distribution. The free radical catalyst is usually present in an amount from 0.003 to 0.1 percent by weight of the polymerization mixture. Representative free radical catalytic initiators are ammonium persulfate (AP); or other inorganic persulfate, benzoyl peroxide, t-butyl peroctoate, isopropyl percarbonate, cumene hydroperoxide, dicumyl peroxide, 1, 3-bis-(t-butylperoxyisopropyl)-benzene, methyl ethyl ketone peroxide, acetyl peroxide, di-t-butylperoxide, t-butyl hydroperoxide, azo compounds such as azodiisobutyronitrile and the like.

Also present in the polymerization mixture is a surface active agent such as sodium dodecyl sulfate (SDS), octylphenocypolyethoxy ethanol, sodium lauryl sulfate, sodium stearate and others. Increasing levels of surface active agent results in smaller bead diameter. However, for biological analytical uses, the surfactant must be removed from the final bead suspension. Therefore, low levels in the range of 0.03 to 0.5 parts by weight of the polymerization mixture are preferred.

The monomers are freshly vacuum distilled before polymerization to remove impurities and inhibitor, if present. The polymerization reaction is preferably conducted in the absence of oxygen, suitably in vacuum or in the presence of an inert gas such as argon. In order to assure uniformity of particle size and to foster uniform initiation throughout the polymerization mixture, the polymerization mixture is intimately stirred before initiation, for example, by tumbling the polymerization container for about 5 minutes before subjecting the mixture to heat.

Initiation is defined as the step of creating a free radical followed by addition of the free radical to an unsaturated bond of the monomer. In the present process, initiation should occur throughout the volume of the polymerization mixture within 10 to 60 seconds of applying heat to the mixture. In the particular embodiment the container is placed in a bath and hot water was added to the bath. The container is then immersed in the hot water and rotated for polymerization.

The temperature of the bath must be at or above the decomposition temperature of the free radical catalyst and suitably at a higher temperature. For example, in the case of ammonium persulfate, initiation at 60° C. will be slow resulting in non-uniformly sized beads having diameters larger than desired. However, initiation at 100° C. results in initiation and propogation at nearly quantitive yield of very small, uniformly shaped particles within about one hour and the size distribution is within ±10% of the average size. Mixing such as by tumbling should continue throughout the polymerization step.

A series of polymerization runs were conducted by adding the monomers, catalyst, ammonium persulfate (AP), and surfactant, sodium dodecyl sulfate (SDS), to 100 cc of distilled water. The polymerization mixture was added to a sealed tumbling container inhibited with argon and tumbled for 4 to 5 minutes before being inserted in a 98° C. bath for one (1) hour. HEMA was distilled in the presence of 0.5% hydroquinone at 95° C., 1 mm Hg pressure; methyl methacrylate (MMA) was distilled at 60° C., 200 mm Hg pressure, methacrylic acid (MAA) was distilled at 60° C., 10 mm Hg pressure; and ethylene glycol dimethacrylate (EGD) was distilled at 98° C., 4 mm, Hg pressure. The amounts of monomer, catalyst, surfactant and the results of the runs are presented in the following table.

these particles measured by transmission electron microscopy is approximately 200 Å smaller than by SEM presumably due to the gold coating used in the latter. It can be approximately calculated that particles with a diameter of 600 Å have 4200 carboxyl groups per particle (based on potentiometric titration and a density of 1.24 gm/cm$^3$) and that each carboxyl group corresponds to an area of 270 square angstroms.

PREPARATION OF FLUORESCENT OR RADIOACTIVE LATEX SPHERES

Tritiated glycine and dansyl-ε-lysine were coupled to copolymer latex spheres (600 A in diameter) by the cyanogen bromide procedure adapted from the method of Cuatrecasas V. Biol. Chem. 1970, 245: 3059. An aqueous suspension of latex spheres (20–55 mg/ml) adjusted to pH 10.5 was activated with CNBr (10–20 mg/ml of suspension) at 25° C. The pH of the reaction mixture was maintained at 10.5 with 1 N NaOH. After 10–15 minutes the activated spheres were added to an equal volume of 5 mM dansyl-ε-lysine or [$^3$H]glycine (1 mCi/μmol) in 0.2 M carbonate buffer at pH 10 and the suspension was stirred for 12 hours at 4° C. Uncoupled reagents were removed by extensive dialysis against several changes of 0.1 M NaCl.

PREPARATION OF DERIVATIZED LATEX SPHERES

Diaminoheptane and ε-aminocaproic acid were

TABLE I

Emulsion Copolymerization of Methacrylates
Percent concentration (W/W)

| Example | HEMA | MMA | MMA | EGD | Total Monomer | SDS | AP | Diameter A | Percent of solod |
|---|---|---|---|---|---|---|---|---|---|
| 1 | 0.9 | 1.59 | 0.3 | 0.21 | 3.0 | 0.120 | 0.013 | 300 | no solid |
| 2 | 2.0 | 3.44 | 0.66 | 0.45 | 6.49 | 0.110 | 0.012 | 600 ± 90 | no solid |
| 3 | 2.1 | 3.71 | 0.7 | 0.49 | 7.0 | 0.110 | 0.012 | 750 ± 100 | no solid |
| 4 | 3.3 | 5.83 | 1.1 | 0.77 | 11.0 | 0.108 | 0.011 | — | no solid |
| 5 | 4.5 | 7.95 | 1.5 | 1.05 | 15.0 | 0.097 | 0.011 | 1400 ± 110 | no solid |
| 6 | 4.8 | 8.48 | 1.6 | 1.12 | 16.0 | 0.097 | 0.010 | 1550 ± 120 | no solid |
| 7 | 7.5 | 13.25 | 2.5 | 1.75 | 25.0 | 0.092 | 0.010 | 2300 ± 170 | 3.2 |
| 8 | 9.0 | 15.90 | 3.0 | 2.1 | 30.0 | 0.086 | 0.009 | 2900 ± 150 | 5.0 |
| 9 | 10.5 | 18.55 | 3.5 | 2.45 | 35.0 | 0.079 | 0.008 | 3400 ± 120 | 6.5 |
| 10 | 3.0 | 5.30 | 1.0 | 0.70 | 10.0 | 0.1 | 0.01 | 1000 ± 60 | no solid |
| 11 | 4.5 | 7.55 | 1.5 | 1.05 | 15.0 | 0.1 | 0.01 | 1400 ± 90 | no solid |
| 12 | 6.0 | 10.60 | 2.0 | 1.40 | 20.0 | 0.1 | 0.01 | 2000 ± 100 | no solid |
| 13 | 7.5 | 13.25 | 2.5 | 1.75 | 25.0 | 0.1 | 0.01 | 2200 ± 100 | 2.2 |
| 14 | 9.0 | 15.90 | 3.0 | 2.10 | 30.0 | 0.1 | 0.01 | 2700 ± 110 | 3.9 |
| 15 | 10.5 | 18.55 | 3.5 | 2.45 | 35.0 | 0.1 | 0.01 | 3300 ± 100 | 4.9 |

Percent solid was the coagulum remaining after filtration of the latex through Whatman No. 1 filter paper. Emulsifier and other ionic impurities were removed from the latex suspension by chromatography on a mixed-bed ion exchange column consisting of Biorad AG 1X10 and AG 50WX12 resins. The concentration of latex particles in solution was based on dry weight analysis. A known volume of solution was dried at 107° C. to constant weight. The density of the latex particles was determined by centrifugation at 100,000 g for 12 h on a linear sucrose gradient. The carboxyl content of the copolymer latex was determined by potentiometric titration. The main components of the aqueous emulsion polymerization system were two water-soluble monomers (HEMA and MAA) and a water-insoluble monomer (MMA) resulting in a high concentration of hydroxyl and carboxyl groups on the surface of the spheres. The actual composition of the polymerizing mixture, the yields and the diameters of particles determined by SEM are shown in Table 1. The diameter of bonded to latex spheres using the aqueous carbodiimide reaction. 10 mg of 1-ethyl-3-(3-dimethyl aminopropyl) carbodiimide (EDC) were added with stirring to 5 ml of latex (25 mg/ml) suspended in 0.01 M diaminoheptane or 0.01 M ε-aminocaproic acid at pH 6–7 and 4° C. After stirring for two hours in the cold, the suspension was exhaustively dialyzed against 0.1 M NaCl.

PREPARATION OF ANTIBODY-LATEX CONJUGATES

For use in cell surface-labeling experiments, purified goat antirabbit IgG antibodies were convalently bonded to latex spheres by either the carbodiimide or glutaraldehyde method. In the carbodiimide reaction 10 mg of EDC were added to 50 mg of ε-aminocaproic acid derivatized latex and 1 mg of antibody in 2 ml of 0.1 M NaCl at pH 7.0 and 4° C. After 2 hours the coupling reaction was stopped by the addition of 0.2 ml of 0.1 M glycrine solution pH 8.0. The glutaraldehyde coupling reaction was carried out in two steps. An aqueous glutaraldehyde solution was added slowly to a suspension of diaminoheptane derivatized latex in 0.01 M sodium phosphate buffer pH 7.0 to give a final concentration of 1.25% glutaraldehyde was removed by overnight dialysis of the latex suspension against 0.1 M NaCl-0.01 M phosphate buffer pH 7.0 at 4° C. Goat antirabbit IgG (1–2 mg) was added to 50 mg of activated latex spheres in 5 ml of 0.01 phosphate buffer at pH 7.0 and the suspension was stirred for 5 hours at 25° C. The antibody latex conjugate was separated from the uncoupled antibody as follows: The reaction suspension was layered onto a gradient consisting of a 58% (wt/wt) sucrose solution overlayered with 10% sucrose solution buffered at pH 8.0 with 0.01 M glycine. After centrifugation at 100,000 g for 3 hours in a Beckman SW-27 rotor (Beckman Instruments, Inc., Spinco Div., Palo Alto, Calif.), the latex conjugate was collected at the interface between 58 and 10% sucrose solutions. This procedure was repeated to insure complete removal of unbound antibody. Finally, the antibody latex conjugate was dialyzed extensively against phosphate buffered saline (PBS), at pH 7.4. Large aggregates were removed by centrifugation at 4,000 g for 10 minutes and the conjugate (15–20 mg/ml) was stored at 4° C.

PURIFICATION AN RADIOACTIVE LABELING OF ANTIBODIES

Goat antirabbit IgG was purified from whole serum on an immunoadsorbent consisting of rabbit IgG-bound to Sepharose 4B by the CNBr method. The adsorbed antibodies were eluted with 3 M sodium thiocyanate. Rabbit IgG and purified goat antirabbit IgG were labeled with carrier-free $Na^{125}I$ using lactoperoxidase bound to Sepharose 4B. Protein concentrations were determined from optical density measurements.

ANTIBODY-LATEX CONJUGATES

The presence of hydroxyl and carboxyl functional groups on the spherical latex beads enable antibodies and other molecules containing primary amino groups to be covalently bonded to the beads. In applications as immunochemical reagents for fluorescent and electron microscopy and for quantitative studies, antibody-latex conjugates can be prepared according to the scheme in FIG. 1. Copolymer latex beads (600 Å in diameter) activated with cyanogen bromide were labeled with either tritiated glycine or dansyl-ε-lysine under conditions which yield a high degree of labeling as shown in the following table.

TABLE II

Bonding of [$^3$H] Glycine to Latex Spheres at 4° C.

| Glycine concn | EDC concn | Time | Buffer | pH | [$^3$H] Glycine incorporation | |
|---|---|---|---|---|---|---|
| mol/liter | mg/ml | h | mol/liter | | nmol/mg | mol/mol* |
| Carbodiimide reaction | | | | | | |
| 0.01 | 2.0 | 1 | — | 6.0 | 0.330 | 27.5 |
| 0.01 | 2.0 | 3 | — | 6.0 | 0.550 | 45.8 |
| 0.001 | 2.0 | 1 | — | 6.0 | 0.036 | 3.0 |
| 0.01 | 20.0 | 1 | — | 6.0 | 0.775 | 64.5 |
| 0.01 | 2.0 | 1 | 0.1 HEPES | 6.0 | 0.315 | 26.2 |
| 0.01 | 2.0 | 1 | 0.1 HEPES | 7.0 | 0.150 | 12.5 |
| 0.01 | — | 3 | | 6.0 | 0.008 | 0.67 |
| CNBr reaction++ | | | | | | |
| 0.01 | | 1 | 0.1 M carbonate | 10.0 | 5.920 | 493.0 |
| 0.01 | | 4 | 0.1 M carbonate | 10.0 | 8.700 | 725.0 |
| 0.01 | | 8 | 0.1 M carbonate | 10.0 | 9.520 | 795.0 |
| 0.01 | | 1 | 0.1 M phosphate | 7.0 | 0.232 | 19.3 |
| 0.01 | | 4 | 0.1 M phosphate | 7.0 | 0.527 | 44.0 |
| 0.01 | | 8 | 0.1 M phosphate | 7.0 | 0.850 | 70.7 |

*Moles of [$^3$H] glycine incorporated per mole of latex sphere is based on an average diameter of 600 Å and a density of 1.24.
++Latex spheres activated for 10 min with 10 mg/ml of CNBr at 25° C. and pH 10.5. Coupling reaction was subsequently carried out at 4° C.

The tagged spheres were subsequently derivatized with either ε-amino-caproic acid or diamino-heptane using the carbodiimide method. Such spacer molecules which extend functional groups used in protein coupling reactions from the insolubilized matrix have been found useful in the purification of proteins by affinity chromatography.

Finally, antibody molecules were conjugated to underivatized or ε-amino-caproic acid derivatized latex spheres by the carbodiimide reaction or to diaminoheptane derivatized spheres by the glutaraldehyde reaction.

A linear dependence was observed when these reactions were carried out at pH 7 for one hour at 4° C. Under these conditions glutaraldehyde coupling of rabbit IgG to spheres previously derivatized with diaminoheptane was most effective and on the basis of a sphere diameter of 600 Å and a density of 1.24 mg/ml, over 8 antibody molecules were bound per latex sphere at rabbit IgG and glutaraldehyde concentrations of 1 mg/ml and 1.25%, respectively. The low amount of protein bound by the CNBr method was due in part to the low efficiency of this reaction at neutral pH (Table II). As in the case of [$^3$H]glycine, binding of rabbit IgG in the absence of coupling reagent was low.

BONDING OF [$^{125}$I] RABBIT IgG

The effect of rabbit IgG concentration on the bonding of [$^{125}$I] rabbit IgG to copolymer acrylic latex spheres 600 Å in diameter by the cyanogen bromide, carbodiimide and glutaraldehyde reactions is shown in FIG. 2. Reactions were carried out at 4° C. for one hour. In the CNBr reaction the latex spheres were initially activated with 20 mg/ml CNBr at pH 10.5 and subsequently coupled to rabbit IgG in 0.1 M phosphate buffer at pH 7.0. The carbodiimide reaction was carried out at pH 7.0 in the absence of added buffer using a final EDC concentration of 2 mg/ml. In the glutaraldehyde reaction rabbit IgG was coupled to diaminoheptane derivatized latex spheres in 0.1 M phosphate buffer at pH 7.0 in the presence of 1.25% glutaraldehyde. The control experiment was carried out in the absence of coupling reagents.

LABELING OF CELLS WITH IMMUNOLATEX SPHERES

The application of latex spheres as quantitative reagents and visual markers for cell surface antigens was demonstrated on red blood cells and lymphocytes using the indirect immunochemical technique. Immunolatex conjugates consisting of an average of 1–2 molecules of goat antirabbit IgG per latex sphere of 600 Å diameter were used in these labeling studies. [$^{125}$I] goat antirabbit IgG antibodies were used to measure the number of molecules bound per latex sphere.

Figure 3:
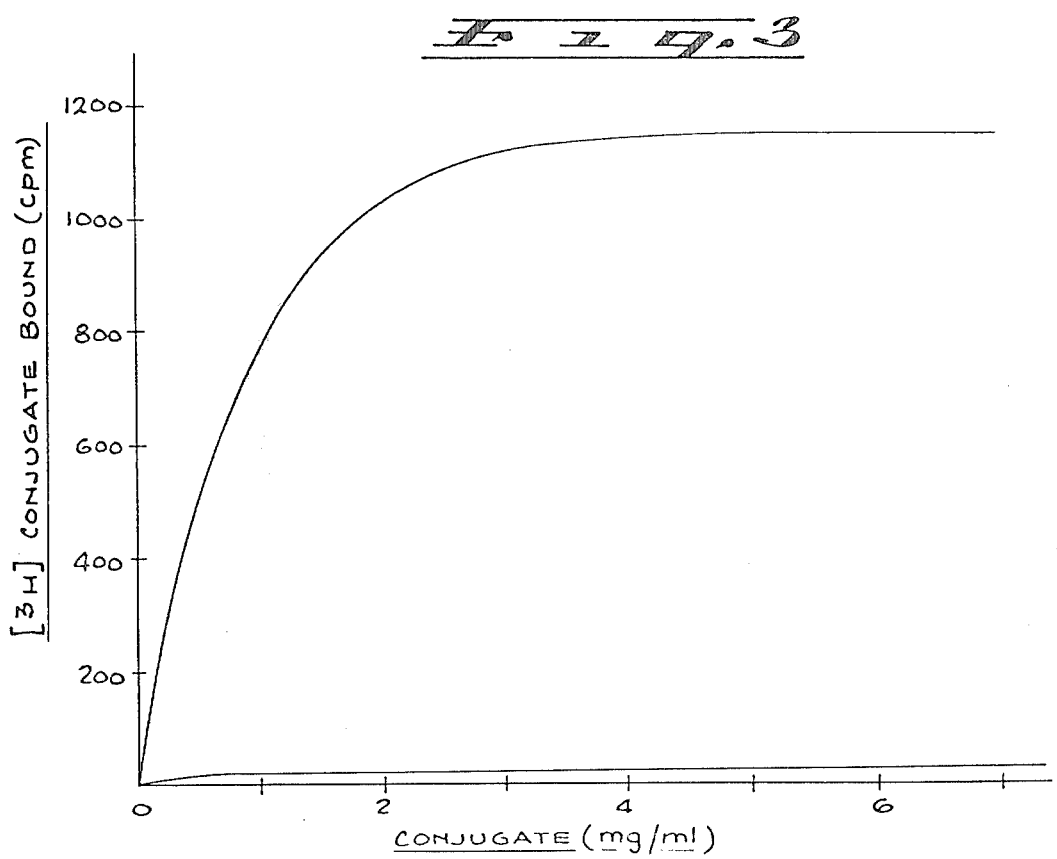
FIG. 3 is a graph showing the effect of goat antirabbit IgG-latex conjugate concentration on the binding of tritiated conjugates to sensitized red blood cells (RBC).

Red Blood Cells: The binding of [$^3$H] glycine labeled immunolatex particles to $2.2 \times 10^6$ human red blood cells sensitized with heterologous rabbit anti-human red blood cell antibodies is shown in FIG. 3. At goat antirabbit IgG-latex concentrations greater than 3 mg/ml, a saturating value of $3.5 \pm 0.5 \times 10^4$ conjugates per cell is reached (calculated from FIG. 3). It can be calculated that a maximum of $4.7 \times 10^4$ spheres of diameter 600 Å can be distributed in a monolayer on a red blood cell of surface area 145 $\mu m^2$(32). SEM micrographs of red blood cells or lymphocytes labeled with particles at saturating goat antirabbit IgG-latex concentrations confirm the tight packing of the spheres on the cell surface. Red blood cells tagged with immunolatex spheres 300 Å in diameter indicate that spheres of this size can also serve as visual markers for SEM. In the control experiments, nonspecific binding of goat antirabbit IgG-latex conjugates to unsensitized red blood cells was generally quite low as determined either by radioactivity measurements (FIG. 3) or SEM visualization.

A new class of immunochemical reagents consisting of antibodies covalently bonded to polymeric microspheres has been prepared and shown to serve as convenient markers for the detection of cell surface antigens by scanning electron microscopy. These reagents have been used to locate antigens on red blood cells and Ig receptors on the surface of mouse spleen lymphocytes.

The specially designed microspheres containing 2-hydroxyethyl methacrylate and methacrylic acid have hydroxyl and carboxyl groups on their surface. These hydrophilic and negatively-charged groups prevent the spheres from binding nonspecifically to cell surfaces and inhibit aggregation of the spheres at neutral pH. The presence of negative charges on the surfaces of the spheres can be inferred from the fact that particle aggregation occurs over a pH range over which the carboxyl groups titrate, as well as in the presence of high concentrations of divalent cations. These functional groups were also necessary for the chemical bonding of proteins and other molecules of biochemical interest to the spheres.

These new reagents offer a number of advantages and applications for the study of cell surface, for immunodiagnosis and immunotherapy:

1. Latex spheres can be synthesized in a wide range of sizes and compositions to suit particular requirements and can be stored indefinitely.
2. Biological molecules such as antibodies, lectins, hormones, and toxins can be bound to the latex spheres by any of a variety of standard chemical procedures for use in the identification of specific populations of cells, as well as in the detection and localization of specific cell surface receptors.
3. Different sizes of spheres can be used in multiple labeling experiments and in conjunction with different types of microscopy. For example, acrylic spheres the size of ferritin and hemocyanin, i.e., 150–350 Å in diameter, can serve as markers for transmission electron microscopy as well as in high resolution scanning electron microscopy; spheres larger than 0.2$\mu$ in diameter can be used with ordinary light microscopy.
4. These microspheres can serve as highly sensitive fluorescent probes and quantitative reagents for biochemical and immunological studies. Binding fluorescent dyes or radioactive molecules to the microspheres instead of to the antibodies permits a high degree of tagging without adversely affecting the antibody activity.

It is to be realized that only preferred embodiments of the invention have been described and that numerous substitutions, alterations and modifications may be made without departing from the spirit and scope of the invention as defined in the following claims.

What is claimed is:

1. A method of forming a protein specific reagent comprising the step of covalently bonding a conjugate of the protein to polymeric beads having a diameter below 3500 Å and comprising
   the copolymer of an addition polymerized, ethylenically unsaturated monomer mixture comprising in percent by weight:
   25–50% by weight of a freely water-soluble monoethylenically unsaturated monomer substituted with a covalent bonding group selected from carboxyl, amino or hydroxyl;
   5–20% by weight of a polyunsaturated cross-linking agent; and
   40–70% by weight of at least one sparingly, water-soluble, ethylenically unsaturated, second monomer having hydrophobic characteristics.

2. A method according to claim 1 further including the step of adding the bead-tagged conjugate to the protein and binding the protein to the conjugate.

3. A method according to claim 1 in which the freely water-soluble monomer is an acrylic monomer.

4. A method according to claim 3 in which the freely water-soluble monomer is present in the monomer mixture in an amount from 30–40% by weight and is selected from acrylamide, hydroxy-lower alkyl acrylates, amino-lower alkyl acrylates, acrylic acid or methacrylic acid.

5. A method according to claim 4 in which the freely water-soluble monomer is hydroxyethylmethacrylate.

6. A method according to claim 5 in which the cross-linking agent is present in an amount of 6–12 percent of the monomer mixture and is a diene or triene capable of addition polymerization with the first and second monomer.

7. A method according to claim 5 in which the cross-linking agent is selected from ethylene dimethacrylate, divinyl benzene, trimethylol propane trimethacrylate, N,N'-methylene bis acrylamide and piperazine-ethylmethacrylate.

8. A method according to claim 5 in which the second monomer comprises a lower $C_1$ to $C_8$ alkyl acrylate.

9. A composition of matter comprising polymeric beads covalently bonded to a conjugate of a protein, said beads having a diameter below 3500 Å and comprising a copolymer of the addition polymerized, ethylenically unsaturated monomer mixturre comprising in percent by weight:
   25–50% of a freely water-soluble monoethylenically unsaturated monomer substituted with a covalent bonding group selected from carboxyl, amino or hydroxyl;

5-20% by weight of a polyunsaturated cross-linking agent; and 40-70% by weight of at least one sparingly, water-soluble, ethylenically unsaturated, second monomer having hydrophobic characteristics.

10. A composition according to claim 9 in which the freely water-soluble monomer is an acrylic monomer.

11. A composition according to claim 10 in which the freely water-soluble monomer is present in the monomer mixture in an amount from 30–40% by weight and is selected from acrylamide, hydroxy-lower alkyl acrylates, amino-lower alkyl acrylates, acrylic acid or methacrylic acid.

12. A composition according to claim 11 in which the freely water-soluble monomer is hydroxyethylmethacrylate.

13. A composition according to claim 12 in which the cross-linking agent is present in an amount of 6–12 percent of the monomer mixture and is a diene or triene capable of addition polymerization with the first and second monomer.

14. A composition according to claim 13 in which the cross-linking agent is selected from ethylene dimethacrylate, divinyl benzene, trimethylol propane trimethacrylate, N,N'-methylene bis acrylamide and piperazine-ethylmethacrylate.

15. A composition according to claim 14 in which the second monomer comprises a lower $C_1$ to $C_8$ alkyl acrylate.

16. A composition according to claim 9 in which the conjugate is selected from the group consisting of antigens, antibodies, hormones, toxins or lectins.

17. A method according to claim 1 in which the beads have a diameter from 100 Å to 2000 Å.

18. A composition according to claim 9 in which the beads have a diameter from 100 Å to 2000 Å.